United States Patent
Ramachandran et al.

(10) Patent No.: US 9,844,361 B2
(45) Date of Patent: Dec. 19, 2017

(54) PULMONARY ULTRASOUND TECHNIQUES FOR ELASTOGRAPHY IN LUNGS

(71) Applicant: KONINKLIJKE PHILIPS N.V., Eindhoven (NL)

(72) Inventors: Bharat Ramachandran, Morganville, NJ (US); Christopher Stephen Hall, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 93 days.

(21) Appl. No.: 14/403,375

(22) PCT Filed: May 27, 2013

(86) PCT No.: PCT/IB2013/054362
§ 371 (c)(1),
(2) Date: Nov. 24, 2014

(87) PCT Pub. No.: WO2013/179203
PCT Pub. Date: Dec. 5, 2013

(65) Prior Publication Data
US 2015/0150536 A1  Jun. 4, 2015

Related U.S. Application Data

(60) Provisional application No. 61/652,352, filed on May 29, 2012.

(51) Int. Cl.
*A61B 8/00* (2006.01)
*A61B 8/08* (2006.01)
(Continued)

(52) U.S. Cl.
CPC ............ *A61B 8/485* (2013.01); *A61B 5/0051* (2013.01); *A61B 5/0095* (2013.01); *A61B 5/085* (2013.01);
(Continued)

(58) Field of Classification Search
CPC .. A61B 5/05; A61B 5/055; A61B 8/00; A61B 8/08; A61B 8/48; A61B 5/0093; A61B 5/4523; A61B 8/5223
See application file for complete search history.

(56) References Cited

U.S. PATENT DOCUMENTS 5,810,731 A  9/1998 Sarvazyan et al.
6,176,827 B1  1/2001 Cohen-Baerie et al.
(Continued)

FOREIGN PATENT DOCUMENTS

CN  1240123 A  1/2000
CN  102359989 A  2/2012
(Continued)

OTHER PUBLICATIONS

Layton, J. "Will elastography replace biopsies for confirming a cancer diagnosis?" Dec. 6, 2006. HowStuffWorks.com < http://health.howstuffworks.com/medicine/tests-treatment/elastography.htm> Oct. 16, 2014.
(Continued)

*Primary Examiner* — Joel Lamprecht

(57) ABSTRACT

A system for pulmonary elastography includes an ultrasound probe (120) configured to evaluate tissue of a target area by transmitting a signal and receiving a response. A contact device (126) is coupled to the ultrasound probe to provide contact between the ultrasound probe and the tissue. An image processing module (110) is configured to output one or more elastograms according to the response.

19 Claims, 6 Drawing Sheets

Figure 1:
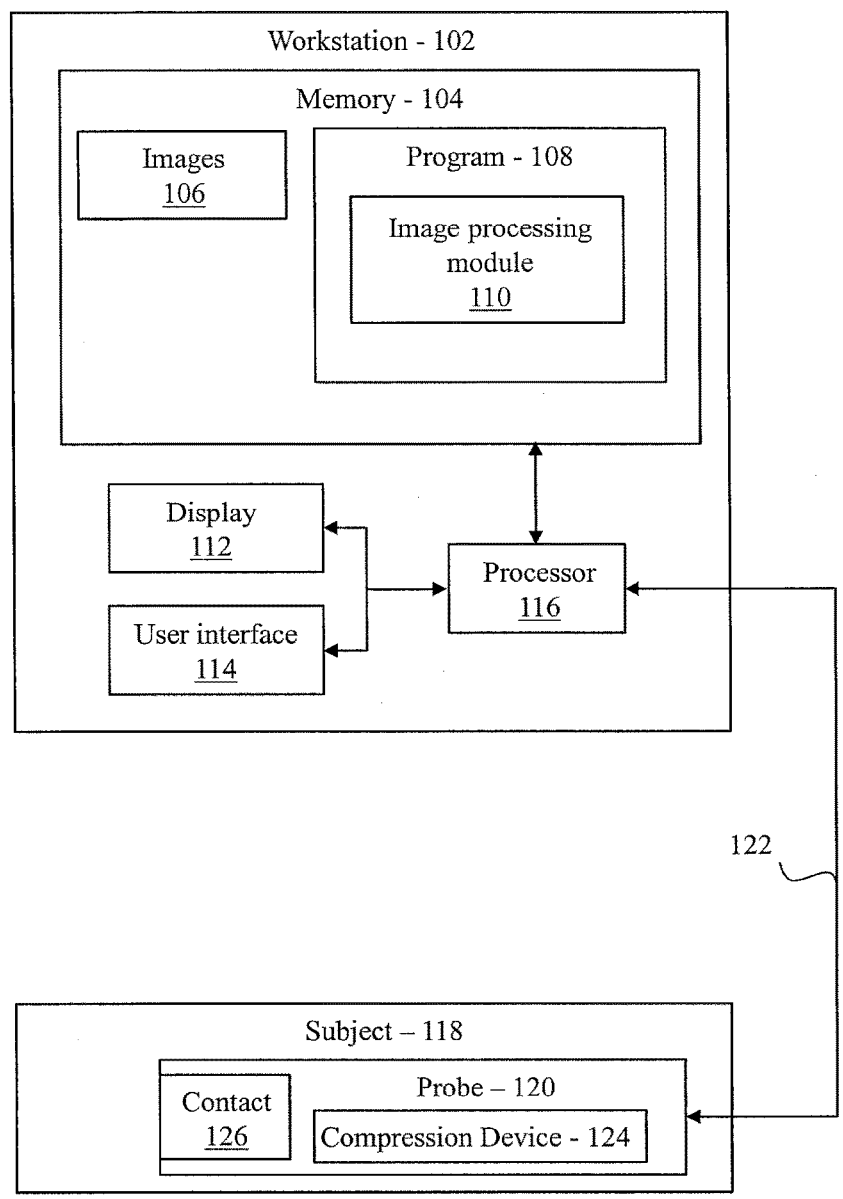

(51) Int. Cl.
  *A61B 8/12* (2006.01)
  *A61B 5/00* (2006.01)
  *G01S 7/52* (2006.01)
  *G01S 15/89* (2006.01)
  *A61B 5/085* (2006.01)

(52) U.S. Cl.
  CPC ............... *A61B 8/085* (2013.01); *A61B 8/12* (2013.01); *A61B 8/4444* (2013.01); *G01S 7/52042* (2013.01); *G01S 15/899* (2013.01); *A61B 8/445* (2013.01)

(56) References Cited

U.S. PATENT DOCUMENTS

| | | | | |
|---|---|---|---|---|
| 8,939,970 | B2* | 1/2015 | Stone | A61B 18/1492 600/372 |
| 2003/0100843 | A1* | 5/2003 | Hoffman | A61B 5/0809 600/538 |
| 2009/0264768 | A1* | 10/2009 | Courtney | A61B 5/0062 600/463 |
| 2010/0081935 | A1 | 4/2010 | Matsumura et al. | |
| 2011/0004104 | A1 | 1/2011 | Sandrin | |
| 2012/0123263 | A1 | 5/2012 | Osaka et al. | |
| 2013/0023729 | A1* | 1/2013 | Vazales | A61B 1/0669 600/104 |
| 2015/0150536 | A1 | 6/2015 | Ramachandran et al. | |

FOREIGN PATENT DOCUMENTS

| | | |
|---|---|---|
| EP | 2060233 A1 | 5/2009 |
| JP | H03146042 A | 6/1991 |
| JP | 2000023978 A | 1/2000 |
| JP | 2010082337 A | 4/2010 |
| WO | 2010012092 A1 | 2/2010 |

OTHER PUBLICATIONS http://usa.autodesk.com/adsk/servlet/pc/index?siteID=123112&id=13773836.

Nguyen, M.M. et al. "Pulmonary ultrasound elastography: a feasibility study with phantoms and ex-vivo tissue". Proceedings of SPIE, vol. 8675, (2013) pp. 867503-867503-9.

Barr, R. G. et al. "Shear wave ultrasound elastography of the prostate—initial results", Ultrasound Quarterly, vol. 28, No. 1, Mar. 1, 2012, pp. 13-20.

* cited by examiner

PULMONARY ULTRASOUND TECHNIQUES FOR ELASTOGRAPHY IN LUNGS

This application is a national stage application under 35 U.S.C. §371 of International Application No. PCT/IB2013/054362 filed on May 27, 2013 and published in the English language on Dec. 5, 2013 as International Publication No. WO/2013/179203, which claims priority to U.S. Application No. 61/652,352 filed on May 29, 2012, the entire disclosures of which are incorporated herein by reference.

This disclosure relates to ultrasound-based elastography and more particularly to pulmonary ultrasound techniques for elastography in lungs.

Lung cancer is one of the most aggressive forms of cancer. The aggressive nature of lung cancer results in a poor prognosis and an alarmingly low survival rate. Therefore, early diagnosis, accurate staging, and timely treatment are critical for the improved treatment of lung cancer. However, the current clinical workflow for the diagnosis and treatment of lung cancer is complex and time-consuming. This slow and complex workflow not only adds to the anxiety of the patient, but also increases the chance of mortality due to the delay in the diagnosis and therapy of lung cancer.

Elastography uses stiffness or strain images of soft tissue to effectively and efficiently diagnose cancer. However, elastography has not been applied to detect and diagnose lung cancer due to the inherent limitations of ultrasound in air. Ultrasound machines are calibrated to perform optimally for imaging tissues. Because the speed of sound in air is very different, air cavities and air spaces within the lungs are not seen in an ultrasound image.

In accordance with the present principles, a system for pulmonary elastography includes an ultrasound probe configured to evaluate tissue of a target area by transmitting a signal and receiving a response. A contact device is coupled to the ultrasound probe to provide contact between the ultrasound probe and the tissue. An image processing module is configured to output one or more elastograms according to the response.

A system for pulmonary elastography includes an ultrasound probe configured to evaluate tissue of a target area by transmitting a signal and receiving a response. A compression device is configured to generate a compression on the tissue, wherein the compression device includes an expandable volume coupled with the ultrasound probe to provide contact between the ultrasound probe and the tissue. An image processing module is configured to output one or more elastograms according to the response.

A method for performing pulmonary elastography includes evaluating tissue of a target area using an ultrasound probe by transmitting a signal and receiving a response. A contact device coupled to the ultrasound probe is employed to provide contact between the ultrasound probe and the tissue. One or more elastograms is outputted according to the response.

These and other objects, features and advantages of the present disclosure will become apparent from the following detailed description of illustrative embodiments thereof, which is to be read in connection with the accompanying drawings.

Figure 2:
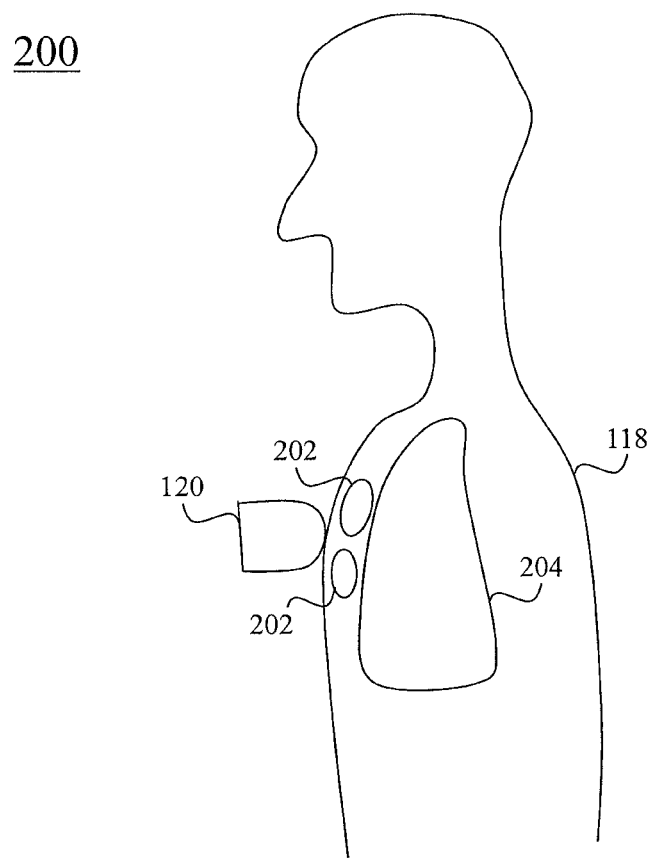
Figure 3:
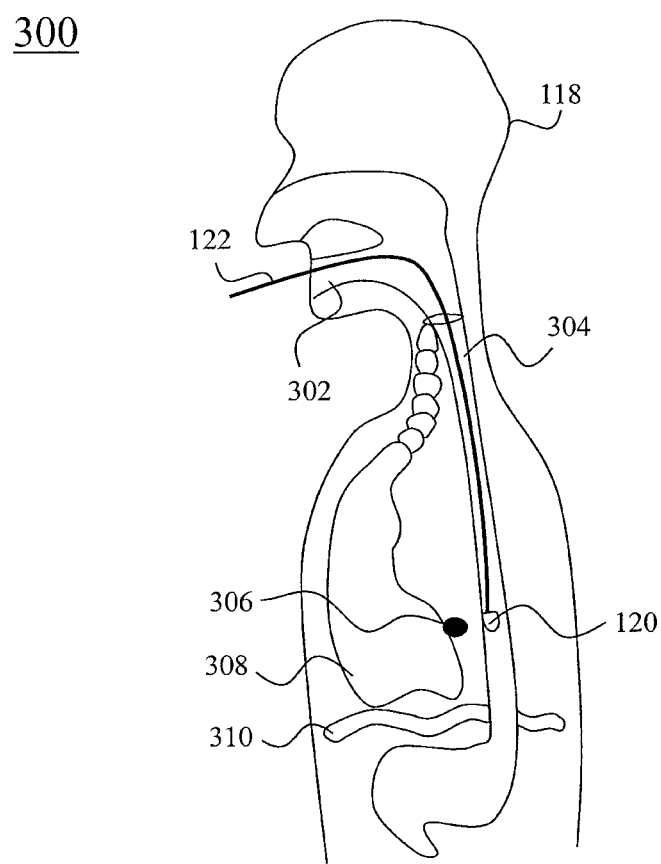
Figure 4:
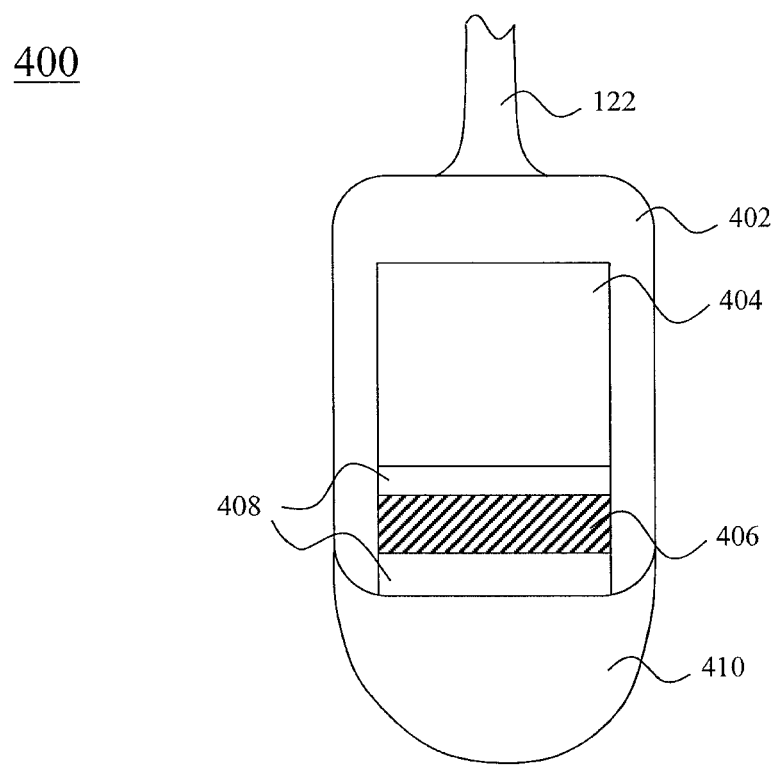
Figure 5:
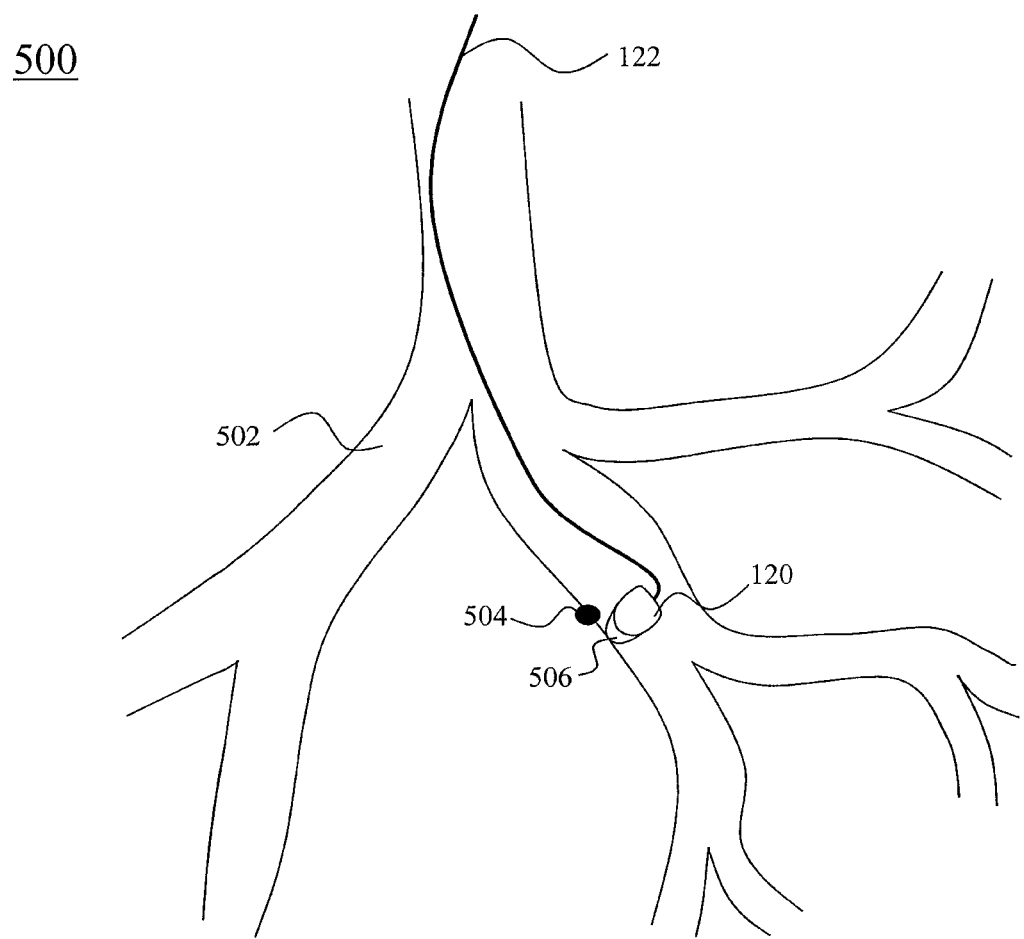
Figure 6:
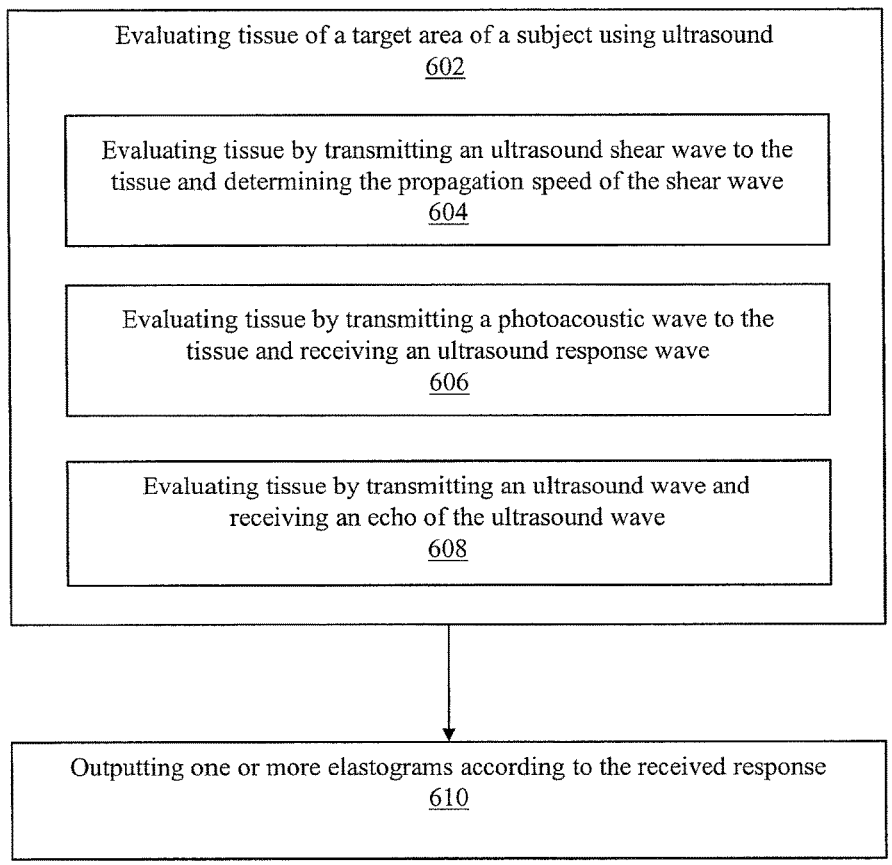

This disclosure will present in detail the following description of preferred embodiments with reference to the following figures wherein:

FIG. 1 is a block/flow diagram showing an ultrasound-based elastography system in accordance with one embodiment;

FIG. 2 illustratively depicts a cross sectional view of a subject with an elastography system applied non-invasively in accordance with one embodiment;

FIG. 3 illustratively depicts cross sectional view of a subject with an elastography system applied minimally invasively in accordance with one embodiment;

FIG. 4 illustratively depicts an ultrasound probe in an elastography system employing a balloon in accordance with one embodiment;

FIG. 5 illustratively depicts an elastography system applied to the airways of a subject according to one embodiment; and FIG. 6 is a block/flow diagram showing a method for ultrasound-based elastography in accordance with one embodiment.

In accordance with the present principles, systems and methods for elastography, and in particular pulmonary elastography, are provided. Elastography uses stiffness-based imaging to diagnose cancer, as cancerous tissue is known to be significantly stiffer than normal, healthy tissue and benign lesions. In one embodiment, tissue may be evaluated by transmitting one or more push pulses to the tissue resulting in an ultrasound shear wave and determining the propagation speed of the shear wave. The shear waves may be modified to account for the lack of shear in an air cavity. The speed of propagation may be used to quantify stiffness. In another embodiment, tissue may be evaluated by transmitting a photoacoustic wave to the tissue and receiving an ultrasound response wave. Evaluating using photoacoustic waves may be performed for the tissue in a natural state and for the tissue in a compressed state. Evaluating using photoacoustic waves may also be performed once, where the tissue can be either in a natural state or a compressed state. In yet another embodiment, tissue may be evaluated by transmitting an ultrasound wave to the tissue and receiving an echo of the ultrasound wave. Preferably, tissue is evaluated by transmitting an ultrasound signal for the tissue in a natural state and a compressed state.

The compression of tissue may be due to the motion of the body, in one embodiment. The motion of the body may include physiological motion such as respiratory motion, including, e.g., the expansion and compression of the lungs or the up and down movement of the diaphragm. In another embodiment, the motion of the body may include employing a ventilator to generate the motion of the body. In other embodiments, compression of the tissue is due to a compression device. The compression device may include a pulsing balloon to generate a compression on the tissue. Other methods of generating compression are also contemplated.

Advantageously, the present principles may provide for the fast and efficient diagnosis of lung cancer using elastography. This may reduce or even eliminate the need for a biopsy in the diagnosis of lung cancer. The present principles allow a clinician to determine, with high accuracy and efficiency, not only whether a suspected site is benign or malignant, but the type and stage of the cancer. The early diagnosis of lung cancer may provide for a high possibility of success in treating the lung cancer.

It should be understood that the present invention will be described in terms of medical instruments; however, the teachings of the present invention are much broader and are applicable to any instrument to generate tissue compression. In some embodiments, the present principles are employed in imaging or analyzing complex biological or mechanical systems. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for ultrasound-based elastography is illustratively shown in accordance with one embodiment. Elastography is a technique that uses stiffness or strain to perform imaging on soft tissue. Elastography works on the principle that when a mechanical compression or displacement is applied, a stiffer tissue does not deform as much as the normal, healthy tissue around it. Elastography is particularly effective for the diagnosis of cancer, as cancerous tissue is known to be significantly stiffer than healthy tissue and even benign lesions.

The present principles are preferably applied for the diagnosis and treatment of lung cancer; however, it is noted that the teachings of the present principles are not limited to the imaging of the lungs or the diagnosis of cancer, but rather are much broader and may be applied in various fields for a number of different applications. For example, in one embodiment, the present principles may be applied in plumbing to detect and identify obstructions in the pipes. Other applications are also contemplated within the scope of the present principles.

System 100 may include a workstation or console 102 from which procedures (e.g., elastography) are supervised and managed. Workstation 102 preferably includes one or more processors 116 and memory 104 for storing programs and applications. It should be understood that the functions and components of system 100 may be integrated into one or more workstations or systems.

Memory 104 may also store images 106, such as elastograms derived from one or more ultrasound sensors, such as a probe 120. Workstation 102 may also include one or more displays 112 for viewing images 106 or data from the probe 120 or for showing results of a diagnosis to a user (e.g., clinician). The display 112 may also permit a user to interact with the workstation 102 and its components and functions. This is further facilitated by a user interface 114, which may include a keyboard, mouse, joystick, or any other peripheral or control to permit user interaction with workstation 102.

The probe 120 is coupled to workstation 102 through cabling 122. The cabling 122 may include electrical connections, instrumentation, etc., as needed. The probe 120 may include one or more of a transceiver, transducer, receiver, other instrumentation, etc. In a preferred embodiment, the probe 120 is an ultrasound probe. It is noted that the probe 120 is not limited to an ultrasound probe, but may include any imaging device or instrumentation. The probe 120 may include a radial probe or a convex probe depending on the location of the target area to be evaluated.

The probe 120 may be used to evaluate a subject 118 (e.g., patient). For example, the probe 120 may evaluate inside, around and outside pulmonary regions of a subject 118. Pulmonary regions include the lungs, airways, lymph nodes, pleural cavity, etc.

Referring for a moment to FIG. 2, with continued reference to FIG. 1, a cross sectional view of a subject 200 with a pulmonary elastography system applied non-invasively is illustratively depicted in accordance with one embodiment. The probe 120 is applied externally to the subject 118, such as on the surface of the body of the subject 118. A substance is preferably applied between the probe 120 and the surface of subject 118. The substance may include any substance that provides acoustic coupling, such as a gel substance. The probe 120 may be placed between ribs 202 to generate elastograms of lesions in the in pleural cavity 204. By intelligently positioning and orienting the probe 120, the probe 120 can evaluate pulmonary target areas without passing through an air cavity. This is particularly useful for identifying cancerous tissue in the periphery of the lungs and beyond such as those found in the pleural cavity, chest wall, etc., which may not be easily accessible in minimally-invasive elastography and often necessitate a percutaneous biopsy.

Referring for a moment to FIG. 3, with continued reference to FIG. 1, a cross sectional view of a subject 300 with a pulmonary elastography system applied minimally invasively is illustratively depicted in accordance with one embodiment. Probe 120 may be inserted into subject 118 through the oral cavity 302 to the esophagus 304. Other entrance points and evaluation locations have also been contemplated within the scope of the present principles. Probe 120 is coupled to workstation 102 through cabling 122. Entry through the esophagus 304 may allow easy access to suspected lesions near the chest and surrounding airways, such as a suspected lesion 306 formed on the lungs 308.

In one embodiment, the probe 120 includes a contact device 126 to evaluate tissue of the subject. Because the speed of sound in air is very different, air cavities and air spaces within, e.g., the pulmonary region are not seen in an ultrasound image. By coupling a contact device 126 to the probe 120, the probe 120 can effectively maintain contact with the tissue of the subject within, e.g., the pulmonary region, overcoming the limitation of ultrasound in air. The contact device 126 may provide less abrasive contact to the tissue. The contact device 126 may also contour to the shape of the tissue for increased contact surface area. The contact device 126 may include any device configured to maintain contact with tissue in a target area of a subject 118. In a particularly useful embodiment, the contact device 126 includes an expandable volume, such as an inflatable balloon or a spring device. Other embodiments of contact device 126 are also contemplated.

Referring for a moment to FIG. 4, with continued reference to FIG. 1, a probe employing a balloon 410 in an elastography system is illustratively depicted in accordance with one embodiment. The probe 400 is coupled to a workstation 102 through cabling 122, which may include a power cord. The probe 400 includes insulator 402 with backing material 404, piezoelectric material 406, electrodes 408 and balloon 410. The balloon 410 is configured to maintain contact with tissue of a subject. The balloon 410 may be coupled to an end (e.g., tip) of the probe 400 in an embodiment. In another embodiment, the balloon 410 is located around the body of the probe 400. Other locations of balloon 410 are also contemplated. In another embodiment, the balloon 410 is filled with a substance that can be safely used within the body of a subject 118 and provides acoustic coupling, such as water or a saline solution. The system 100 may also include a controller device configured to adjust the pressure of a filled balloon 410. The controller may include a knob, switch, etc. to increase or decrease the pressure of the balloon 410 to, e.g., contour to the shape of the tissue. Increasing or decreasing pressure may include adding or releasing the filled substance. In other embodiments, the balloon 410 is not filled.

Referring back to FIG. 1, pulmonary elastography system 100 may be configured to perform pulmonary elastography by: transmitting one or more push pulses resulting in a shear wave and determining the speed of propagation of the shear wave; by transmitting a photoacoustic wave and receiving an ultrasound response; and by transmitting an ultrasound wave and receiving the echo. Other implementations of pulmonary elastography are also contemplated within the scope of the present principles.

In accordance with one embodiment, the pulmonary elastography system 100 is configured to evaluate tissue by determining the propagation speed of shear waves. The probe 120 is configured to transmit one or more ultrasound push pulses to tissue of the target area, which results in vibration applied in the direction of the push pulse wave and a shear wave perpendicular to the direction of transmission. The shear waves may be modified to account for air cavities. For example, the frequency of the push pulse wave or the coupling properties of the push pulse wave may be modified. Other modifications are also contemplated. As the shear waves propagate throughout the target area, a second probe 120 (e.g., ultrasound scanner) can measure the speed of propagation. Based on the propagation speed, tissue stiffness may be quantified.

In accordance with another embodiment, the pulmonary elastography system 100 is configured to evaluate tissue by transmitting a photoacoustic wave to tissue of the target area and receiving an ultrasound wave. Photoacoustic waves may include light waves (e.g., non-ionizing laser). Tissue of the target area absorbs some of the energy from the photoacoustic waves, which is converted into heat, resulting in the emission of ultrasound waves. Advantageously, photoacoustic waves are not influenced by air and, thus, overcome the limitations of acoustic coupling with air. In some embodiments, the tissue of the target area may be evaluated when the tissue is in a natural state and when the tissue is in a compressed state. In other embodiments, the tissue of the target area may be evaluated once. The tissue may or may not be compressed. The evaluated tissue may be compared to a baseline. The baseline may include results of previous trails that are, for example, averaged. Other baseline measurements are also contemplated.

In accordance with yet another embodiment, the pulmonary elastography system 100 is configured to evaluate tissue by transmitting a (e.g., ultrasound) signal and receiving an echo of the signal. Preferably, the tissue is evaluated once in a natural state and once in a compressed state.

As discussed above, some embodiments of the pulmonary elastography system 100 may involve evaluating tissue in a compressed state.

In one embodiment, the probe 120 may evaluate tissue in the target area compressed due to the motion of the body of the subject 118. For example, the motion of the body may be due to physiological motion of the subject 118. Physiological motion may include, e.g., the compression and displacement generated from respiratory motion, such as the expansion and compression of the lungs 308 and the up and down motion of the diaphragm 310 (of FIG. 3), or the motion of internal organs, such as the beating of the heart. Other sources of compression due to physiological motion of a subject 118 are also contemplated. In other embodiments, motion of the body may be due to a device configured to provide body motion. For example, a ventilator may provide a mechanism for breathing for a subject 118 who is unable to sufficiently breathe independently. The ventilator may cause expansion and compression of the lungs 308 and the up and down motion of the diaphragm 310 (of FIG. 3). Other sources of compression due to body motion are also contemplated.

In other embodiments, compression of tissue in the target area is generated using a compression device 124. The compression device 124 may be wholly or partially integrated within the probe 120 in some embodiments. In other embodiments, the compression device 124 and the probe 120 are separate and discrete. The compression device 124 may include any device that is configured to generate a compression or displacement on tissue in a target area of the subject 118.

In an embodiment, the compression device 124 may include an expandable volume, such as an inflatable balloon 410 (FIG. 4). The balloon 410 may be coupled with the probe 400. The balloon 410 may be filled with a substance that can be safely used within the body of a subject 118 and provides acoustic coupling (e.g., water or a saline solution). In a particularly useful embodiment, the balloon 410 may be pulsed using a controller device at amplitudes and frequencies to generate a compression on tissue of a target area. The amplitudes and frequencies may be constant or varying. The amplitudes and frequencies may also be known or random. The pulsing may be performed manually using the controller device. Pulsing may include increasing and decreasing the pressure of the balloon 410 by adding or releasing the filled substance. Referring for a moment to FIG. 5, with continued reference to FIG. 1, pulmonary elastography system is performed in the airways 500 in accordance with one embodiment. The probe 120 is navigated through the airways 502 to detect and identify a suspected lesion 504. The suspected lesion 504 may be located completely within the airways 502, completely outside the airways 502, or partially within and partially outside the airways 502. Other locations of suspected lesions 502 are also contemplated. The probe 120 may include balloon 506 to maintain contact with tissue of the airways 502. Preferably, balloon 506 is pulsed to generate a compression on the tissue and suspected lesion 504.

In another embodiment, the compression device 124 includes the probe 120. A user (e.g., doctor) may apply pressure onto the probe 120 into tissue of a target area to induce compression. In other embodiments, the motion of the probe 120 while navigating on, in or around a subject 118 generates a compression or displacement on tissue of a target area. Using tracking techniques as are known in the art, additional displacement of healthy tissue and lack of additional displacement of cancerous tissue can be observed.

In yet another embodiment, the compression device 124 may include a mechanical device configured to generate mechanical compression and vibrations on tissue of a subject 118. The mechanical device may include a motorized mechanism or a power-driven device.

In still another embodiment, the compression device 124 may apply an acoustic push to a target area of a subject 118 using ultrasound waves in the same direction. The acoustic push may be performed with or without beamforming.

A computer implemented program 108 is stored in memory 104 of workstation 102. The program may include one or more modules, each configured to perform various functions. It should be understood that the modules may be implemented in various combinations of hardware and software.

Program 108 may include the image processing module 110, which is configured to process data received from the probe 120 to generate elastograms (images of tissue strain). In one embodiment, the image processing module 110 is configured to receive the propagation speed of a shear wave. Based on the propagation speed, strain characteristics of tissue may be quantified to output an elastogram. In other embodiments, the image processing module 110 receives ultrasound response signals from the probe 120 from tissue in the target area. The ultrasound response signals may be from, e.g., an echo of a transmitted ultrasound wave or a result of a photoacoustic wave. The image processing module 110 generates elastograms as is known in the art.

In one embodiment, the image processing module 110 outputs an elasticity image. In other embodiments, the image processing module 110 outputs an elastogram depicting absolute strain characteristic of the tissue. The image processing module 110 may also juxtapose the elastogram with colors according to the tissue strain. The image processing module 110 may output the elastogram in real-time or retrospectively. The output may involve one or more displays 112 and user interfaces 114.

Advantageously, the present principles apply ultrasound based elastography to the pulmonary regions of a patient for the diagnosis, classification, staging and treatment of, e.g., lung cancer. The present principles overcome the limitations of ultrasound in air and allow a user to determine, with high accuracy, not only whether a target is benign or malignant, but also the exact type and stage of the cancer. Furthermore, the diagnosis of lung cancer may be performed without the need for a biopsy, which may also lead to a reduction in manual errors by the doctor. The present principles reduce the time for diagnosis and simplify the workflow, which may be critical for a patient given the aggressive nature of lung cancer.

Referring now to FIG. 6, a block/flow diagram showing a method for ultrasound-based pulmonary elastography is illustratively depicted in accordance with one embodiment. In block 602, tissue of a target area of a subject is evaluated using ultrasound.

In one embodiment, evaluating the target area may include coupling a contact device with an ultrasound probe to maintain contact with tissue of the target area, such as the lungs, to overcome the limitations of ultrasound in air. The contact device may be located at an end (e.g., tip) of the probe. In other embodiments, the contact device is located around the body of the probe. Other locations are also contemplated. The contact device may provide less abrasive contact to the tissue and may contour to the shape of the tissue for increased contact surface area. In a particularly useful embodiment, the contact device includes an expandable volume, such as an inflatable balloon; however, other embodiments of the contact device are also contemplated. The balloon may be filled with a substance that can be safely used with the body of the subject and provides acoustic coupling, such as, e.g., water or a saline solution. The pressure of the balloon may be controlled using a controller device to increase or decrease the pressure of the balloon to, e.g., contour to the shape of the tissue. Increasing or decreasing pressure may include adding or releasing the filled substance. In another embodiment, the balloon may not be filled.

Tissue at a target area of a subject may be evaluated non-invasively. A probe may be applied externally to the body of a subject, such as on the chest surface. Preferably, a substance is applied between the ultrasound probe and the surface of the subject. The substance may include any substance which provides for acoustic coupling, such as a gel substance. In yet another embodiment, the ultrasound probe is applied on the chest surface of the body of the subject and directed between a first rib and a second rib to evaluate pulmonary regions of the subject. Pulmonary regions include the lungs, airways, lymph nodes, pleural cavity, etc. The non-invasive evaluation of the target pulmonary region of the subject is particularly effective for identifying lesions in the periphery of the lungs, pleural cavity and chest wall, which may not be accessible in a minimally-invasive approach.

Tissue at the target area of a subject may also be evaluated minimally-invasively. A probe may be applied internally to the subject. For example, the probe may be inserted through the oral cavity of the subject to evaluate lesions in and around the esophagus. This allows access to suspected lesions near the chest and surrounding airways. Other entrance points of the subject have also contemplated to evaluate the target pulmonary region.

In block 604, tissue may be evaluated by transmitting an ultrasound shear wave to the tissue and determining the speed of propagation of the shear wave. One or more ultrasound push pulses may be transmitted to tissue of the target area. The push pulses include a vibration applied in the direction of the wave and a shear wave perpendicular to the direction of transmission. Preferably, the shear waves may be modified to account for air cavities. In one exemplary embodiment, the frequency of the push pulse wave or the coupling properties of the push pulse wave may be modified. Other modifications are also contemplated. As the shear waver propagates throughout the target area, the speed of propagation is used to quantify stiffness of the tissue.

In block 606, tissue may be evaluated by transmitting a photoacoustic wave to the tissue and receiving an ultrasound response wave. Photoacoustic waves may include, e.g., light waves. Tissue of the target area absorbs some of the energy of the photoacoustic wave. The absorbed energy is converted into heat and ultrasound waves are emitted. Photoacoustic waves are not influenced by air and, thus, overcome the limitations of acoustic coupling with air. In one embodiment, tissue is evaluated in a natural state and in a compressed state. In other embodiments, the tissue is evaluated once. The tissue may or may not be compressed.

In block 608, tissue may be evaluated by transmitting an ultrasound wave to the tissue and receiving an echo of the ultrasound wave. Preferably, tissue is evaluated in a natural state and in a compressed state.

As discussed above, particularly with some embodiments of block 606 and 608, tissue may be evaluated in a compressed state.

In one embodiment, tissue of a target area may be evaluated at a compressed state due to motion of the body of the subject. For example, the motion of the body may be due to physiological motion, such as respiratory motion (e.g., expansion and compression of the lungs, up and down motion of the diaphragm) or the motion of internal organs (e.g., beating of the heart). Other sources of compression due to physiological motion are also contemplated. In other embodiments, motion of the body may be due to a device configured to provide body motion. For instance, a ventilator may provide a mechanism for breathing for a subject who is unable to sufficiently breathe independently. The ventilator may cause the expansion and compression of the lungs and the up and down motion of the diaphragm. Other sources of compression due to body motion are also contemplated.

In another embodiment, evaluating tissue at a compressed state may include generating compression on the tissue. For instance, generating compression may include manually pressing the ultrasound probe into tissue of a target area to induce a compression.

In other embodiments, generating compression includes navigating the probe on, in or around the subject. Tracking techniques, as are known in the art, may be applied to observe the additional displacement of healthy tissue and the lack of additional displacement of cancerous tissue.

In yet another embodiment, generating compression may include applying an acoustic push to a target area of a subject. Applying an acoustic push may include applying ultrasound waves in the same direction. The acoustic push may be performed with or without beamforming.

In still another embodiment, generating compression includes employing a compression device. The compression device may be fully or partially integrated within the ultrasound probe. The compression device and the ultrasound probe may also be separate and discrete. The compression device may include any device that generates a compression on tissue.

In an embodiment, the compression device may include an expandable volume, such as an inflatable balloon coupled with the ultrasound probe. The balloon may be filled with a substance that can be safely used within the body and provides acoustic coupling (e.g., water or a saline solution). The balloon may pulse at amplitudes and frequencies. Amplitudes and frequencies of the pulsing may be controlled to be at constant or varying frequencies. The pulsing may be at known amplitudes and frequencies or may be random. The pulsing may also be controlled manually using a controller device. Pulsing may include increasing and decreasing the pressure of the balloon by adding or releasing the filled substance.

In other embodiments, the compression device may include a mechanical device to generate mechanical compression. The mechanical device may include a motorized mechanism or a power-driven device.

In block 610, one or more elastograms are outputted according to the received response. In one embodiment, one or more elastograms are outputted according to the propagation speed of a shear wave (e.g., block 604). Based on propagation speed, strain characteristics of tissue may be quantified. In other embodiment, one or more elastograms is outputted according an ultrasound response signal received from tissue in the target area. The ultrasound response signal may be from, e.g., an echo of a transmitted ultrasound wave (e.g., block 608) or a result of a photoacoustic wave (e.g., block 606). Generating elastograms is performed as is known in the art.

Outputting one or more elastograms may include outputting an elasticity image. In other embodiments, the elastogram may depict absolute strain characteristics of the tissue. In another embodiment, the elastogram may be juxtaposed with colors according to the tissue strain. Elastograms may be outputted in real-time or retrospectively.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for pulmonary ultrasound techniques for elastography in lungs (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for pulmonary elastography, comprising:
  a probe configured to be inserted within an airway of a subject and to evaluate tissue of a target area relative to the airway by transmitting at least one push pulse to the target area resulting in an ultrasound shear wave;
  a contact device coupled to the probe to provide contact between the probe and the tissue;
  an additional probe configured to measure a propagation speed of the ultrasound shear wave, and an image processing module configured to output one or more elastograms according to a measurement of the propagation speed of the ultrasound shear wave by the additional probe.

2. The system as recited in claim 1, wherein the contact device includes an expandable volume.

3. The system as recited in claim 1, wherein the probe is configured to evaluate the tissue under a compression.

4. The system as recited in claim 3, further comprising a compression device configured to generate the compression on the tissue.

5. The system as recited in claim 4, wherein the compression device includes a balloon structured to generate the compression.

6. The system as recited in claim 5, wherein the balloon is configured to pulse to generate the compression.

7. The system as recited in claim 6, wherein the balloon is configured to pulse by adding or releasing a filled substance.

8. The system as recited in claim 6, wherein the balloon is configured to pulse at known frequencies and amplitudes.

9. The system as recited in claim 3, wherein the probe is configured to evaluate the tissue under the compression due to motion of a body.

10. The system as recited in claim 9, wherein the motion of the body includes a physiological motion, the physiological motion including at least one of (i) an expansion and compression of lungs or (ii) an up and down motion of a diaphragm.

11. The system as recited in claim 9, further comprising a ventilator to generate the motion of the body, the motion including at least one of (i) an expansion and compression of lungs or (ii) an up and down motion of a diaphragm.

12. The system as recited in claim 1, further comprising: wherein the image processing module is further configured to modify the ultrasound shear wave to compensate for a lack of shear in an air cavity.

13. A method for performing pulmonary elastography, comprising:
evaluating tissue of a target area using a probe inserted within an airway of a subject and by transmitting at least one push pulse resulting in an ultrasound shear wave;
employing a contact device coupled to the probe to provide contact between the ultrasound probe and the tissue;
providing an additional probe configured to measure a propagation speed of the ultrasound shear wave; and
outputting one or more elastograms according to the propagation speed of the ultrasound shear wave.

14. The method as recited in claim 13, wherein evaluating includes evaluating the tissue under a compression.

15. The method as recited in claim 14, wherein the compression is due to a physiological motion of a body, the physiological motion including at least one of (i) an expansion and compression of lungs or (ii) an up and down motion of a diaphragm.

16. The method as recited in claim 14, further comprising employing a ventilator to generate motion of a body resulting in the compression, the motion including at least one of (i) an expansion and compression of lungs or (ii) an up and down motion of a diaphragm.

17. The method as recited in claim 14, further comprising generating the compression, wherein generating the compression includes pulsing an inflatable volume, and wherein pulsing the inflatable volume includes pulsing a balloon at known frequencies and amplitudes.

18. A system for pulmonary elastography, comprising:
a probe configured be inserted within an airway of a subject and to evaluate tissue of a target area by transmitting at least one push pulse to the target area resulting in an ultrasound shear wave;
a compression device decoupled from the probe to generate a compression on the tissue,
wherein the probe is configured to evaluate the tissue under the compression of the tissue by the compression device;
an additional probe configured to measure a propagation speed of the ultrasound shear wave; and
an image processing module configured to output one or more elastograms according to a measurement of the propagation speed of the ultrasound shear wave by the additional probe.

19. The system as recited in claim 18, wherein the probe is configured to evaluate the tissue under the compression due to motion of a body.

* * * * *